United States Patent
Conrad et al.

(10) Patent No.: US 7,213,599 B2
(45) Date of Patent: *May 8, 2007

(54) AIRWAY IMPLANT

(75) Inventors: Timothy R. Conrad, Eden Prairie, MN (US); Susan L. Critzer, Dellwood, MN (US); Brian J. Erickson, Woodbury, MN (US); Anja K. Metzger, Stillwater, MN (US); John P. Sopp, Forest Lake, MN (US)

(73) Assignee: Restore Medical, Inc., St. Paul, MN (US)

( * ) Notice: Subject to any disclaimer, the term of this patent is extended or adjusted under 35 U.S.C. 154(b) by 343 days.

This patent is subject to a terminal disclaimer.

(21) Appl. No.: 10/877,003

(22) Filed: Jun. 24, 2004

(65) Prior Publication Data

US 2005/0092334 A1 May 5, 2005

Related U.S. Application Data

(63) Continuation-in-part of application No. 10/698,819, filed on Oct. 31, 2003.

(51) Int. Cl.
*A61B 19/00* (2006.01)

(52) U.S. Cl. .................................................. 128/897

(58) Field of Classification Search ........ 128/897–899, 128/846, 848, 859–862; 602/902; 623/9, 623/11.11, 14.11
See application file for complete search history.

(56) References Cited

U.S. PATENT DOCUMENTS

| | | | |
|---|---|---|---|
| 5,843,021 A | 12/1998 | Edwards et al. | |
| 5,979,456 A | 11/1999 | Magovern | |
| 5,988,171 A | 11/1999 | Sohn et al. | |
| 6,161,541 A | 12/2000 | Woodson | |
| 6,216,702 B1 | 4/2001 | Gjersøe | |
| 6,250,307 B1 | 6/2001 | Conrad et al. | |
| 6,408,851 B1 | 6/2002 | Karell | |
| 6,431,174 B1 | 8/2002 | Knudson et al. | |
| 6,523,542 B2 | 2/2003 | Knudson et al. | |
| 6,601,584 B2 | 8/2003 | Knudson et al. | |
| 6,748,950 B2 | 6/2004 | Clark et al. | |
| 2001/0050084 A1 | 12/2001 | Knudson et al. | |
| 2001/0050085 A1 | 12/2001 | Knudson et al. | |
| 2002/0035994 A1 | 3/2002 | Stevens et al. | |

(Continued)

FOREIGN PATENT DOCUMENTS

DE      44 12 190 A1      10/1995

(Continued)

OTHER PUBLICATIONS

Eisle et al., "Direct Hypoglossal Nerve Stimulation in Obstructive Sleep Apnea", *Arch. Otolaryngol. Head Neck Surg.*, vol. 123, pp. 57-61 (1997).

(Continued)

*Primary Examiner*—John P. Lacyk
(74) *Attorney, Agent, or Firm*—Merchant & Gould P.C.

(57) ABSTRACT

Methods and apparatuses are disclosed for treating a condition of a patient's airway. The condition is attributed at least in part to a spacing of tissue from opposing surfaces in the airway. In various embodiments, the base of the tongue including geometry and position of the tongue is altered.

7 Claims, 12 Drawing Sheets

U.S. PATENT DOCUMENTS

| | | |
|---|---|---|
| 2002/0049479 A1 | 4/2002 | Pitts |
| 2004/0045556 A1 | 3/2004 | Nelson et al. |
| 2004/0073272 A1 | 4/2004 | Knudson et al. |
| 2004/0134491 A1 | 7/2004 | Pflueger et al. |
| 2004/0139975 A1 | 7/2004 | Nelson et al. |
| 2004/0149290 A1 | 8/2004 | Nelson et al. |
| 2004/0153127 A1 | 8/2004 | Gordon et al. |

FOREIGN PATENT DOCUMENTS

| | | |
|---|---|---|
| DE | 199 20 114 A1 | 11/2000 |
| EP | 1039859 B1 | 12/1998 |
| WO | WO/2004/021869 A2 | 3/2004 |
| WO | WO/2004/021870 A2 | 3/2004 |
| WO | WO 2005/044158 A1 | 5/2005 |
| WO | WO 2005/082452 A1 | 9/2005 |
| WO | WO 2006/072571 A1 | 7/2006 |

OTHER PUBLICATIONS

Miller et al., "Role of the Tongue Base Suspension Suture with the Repose System Bone Screw in the Multilevel Surgical Management of Obstructive Sleep Apnea", *Otolaryngol. Head Neck Surg.*, vol. 126, pp. 392-398 (2002).

Powell et al., "Radiofrequency Tongue Base Reduction in Sleep-Disordered Breathing: A pilot study", *Otolaryngol. Head Neck Surg.*, vol. 120, pp. 656-664 (1999).

Powell et al., "Radiofrequency Volumetric Reduction of the Tongue—A Porcine Pilot Study for the Treatment of Obstructive Sleep Apnea Syndrome", *Chest*, vol. 111, pp. 1348-1355 (1997).

Thomas, A. et al., "Preliminary findings from a prospective, randomized trial of two tongue-base surgeries for sleep-disordered breathing," *Otolaryngology-Head and Neck Surgery*, vol. 129, No. 5, pp. 539-546 (Nov. 2003).

Ersek et al., "Minimally Invasive Macro Impants," *Worldplast*, vol. 1, No. 4, pp. 275-285 (1996).

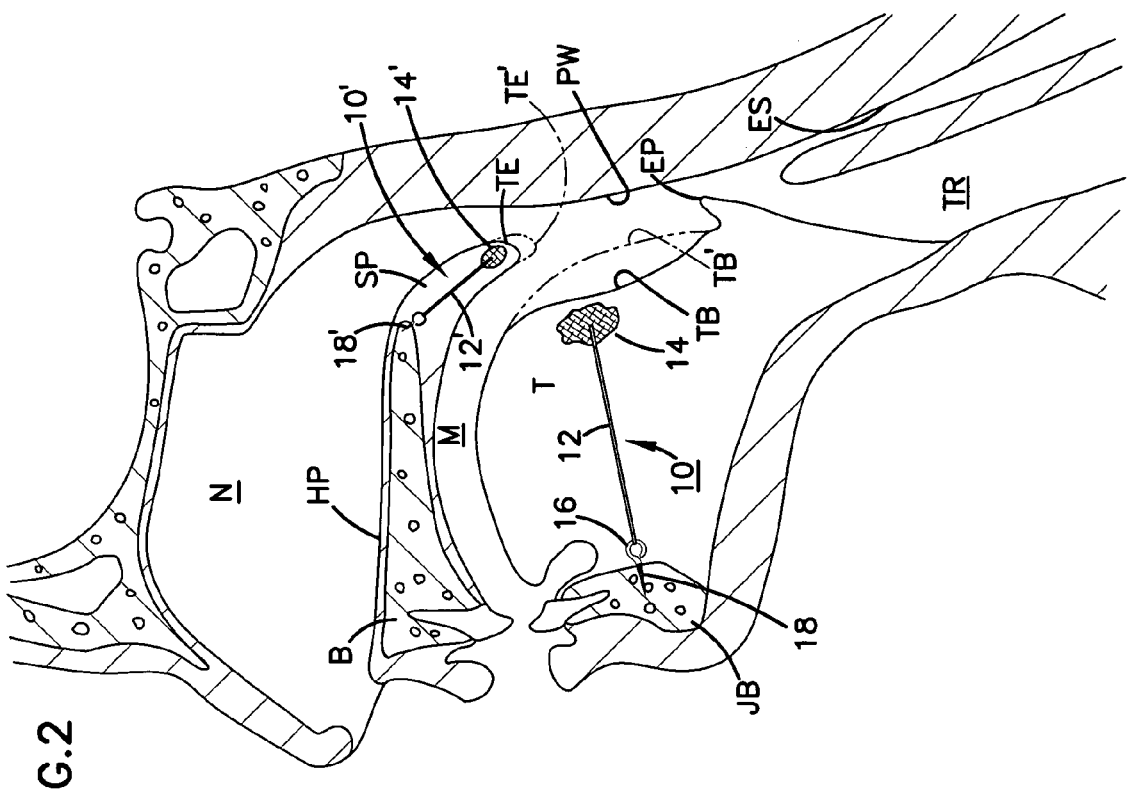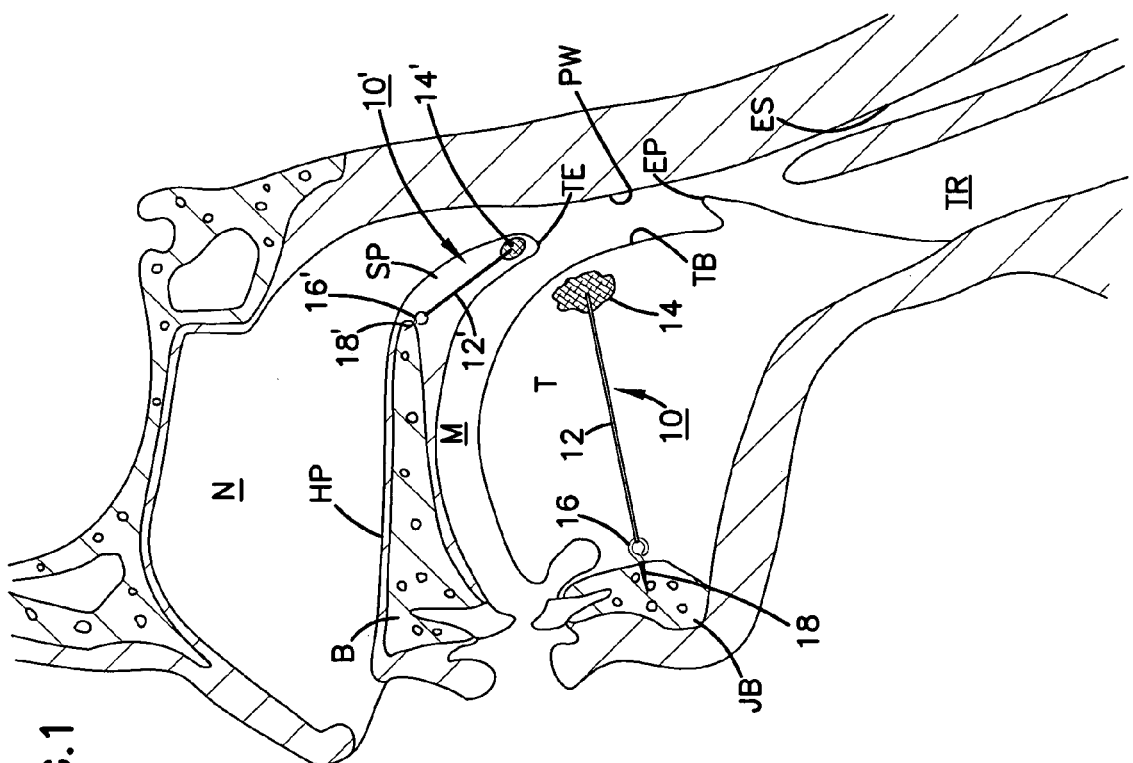

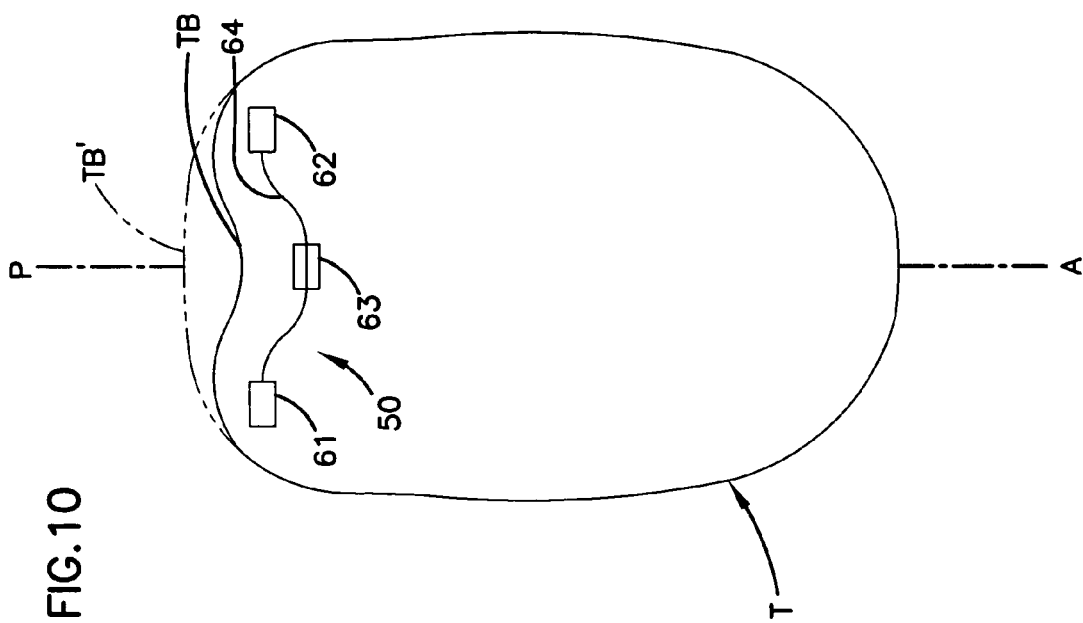
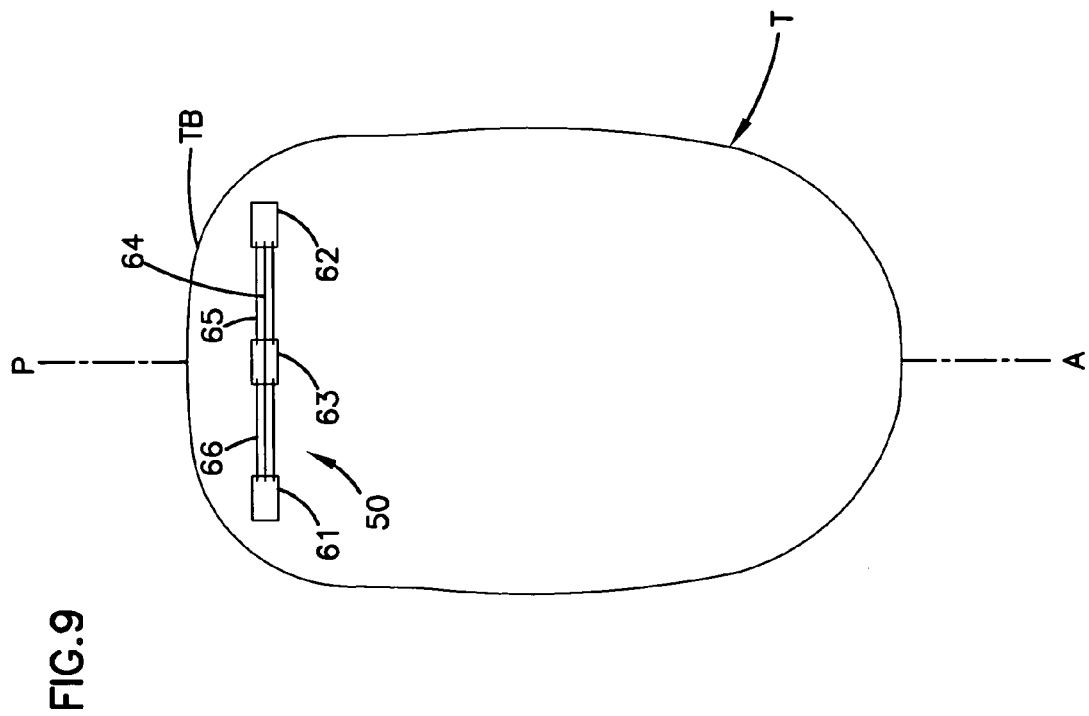

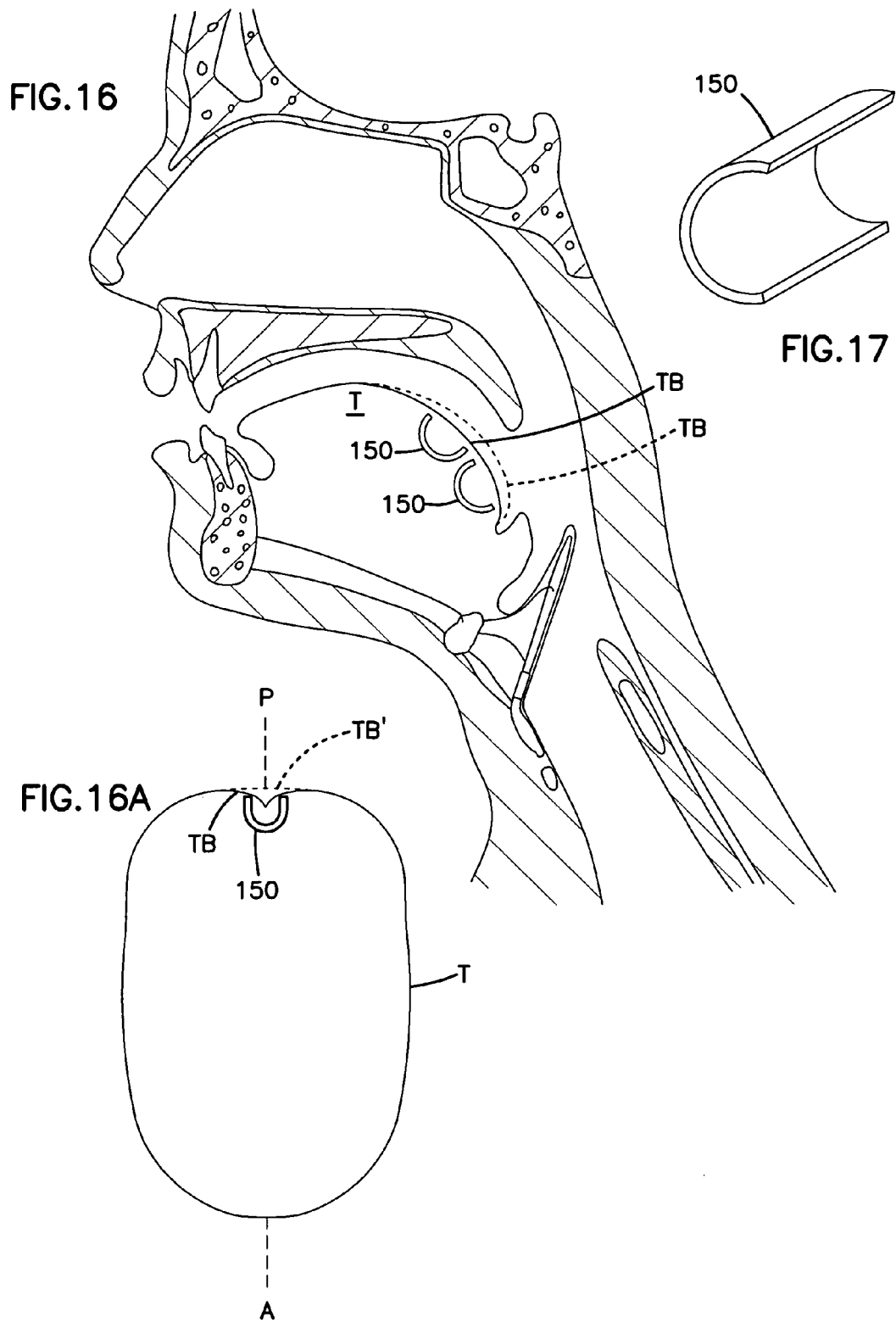

AIRWAY IMPLANT

I. CROSS-REFERENCE TO RELATED APPLICATION

The present application is a continuation-in-part of U.S. patent application Ser. No. 10/698,819 filed Oct. 31, 2003 and entitled "Airway Implant".

II. BACKGROUND OF THE INVENTION

1. Field of the Invention

This invention pertains to a method and apparatus for treating a condition of an upper airway of a patient. More particularly, this invention is directed to such a method and apparatus including an implant to improve patency of the airway.

2. Description of the Prior Art

Upper airway conditions such as obstructive sleep apnea ("OSA") and snoring have received a great deal of attention. These conditions have recognized sociological and health implications for both the patient and the patient's bed partner.

Numerous attempts have been made towards treating OSA and snoring. These include placing implants in either the tissue of the soft palate or the pharyngeal airway as disclosed in commonly assigned U.S. Pat. No. 6,250,307 to Conrad et al. dated Jun. 26, 2003, U.S. Pat. No. 6,523,542 to Metzger et al. dated Feb. 25, 2003 and U.S. Pat. No. 6,431,174 to Knudson et al. dated Aug. 13, 2002. Further, U.S. Pat. No. 6,601,584 to Knudson et al. dated Aug. 5, 2003 teaches a contracting implant for placement in the soft palate of the patient.

In the '584 patent, an embodiment of the contracting implant includes two tissue attachment ends (for example ends 102b in FIGS. 46 and 47) which are maintained in a space-apart, stretched relation by a bio-resorbable member 102c which surrounds an internal spring or resilient member 102a. After implantation, tissue grows into the attachment ends 102b. The bioresorbable member 102c is selected to resorb after the tissue in-growth permitting the resilient member 102a to contract drawing ends 102b together as illustrated in FIG. 47 of the '584 patent (incorporated herein by reference). Tissue contraction is believed to be desirable in that the tissue contraction results in a debulking of the tissue and movement of tissue away from opposing tissue surfaces in the pharyngeal upper airway.

Another prior art technique for treating OSA or snoring is disclosed in U.S. Pat. No. 5,988,171 to Sohn et al. dated Nov. 23, 1999. In the '171 patent, a cord (e.g., a suture material) (element 32 in FIG. 6 of the '171 patent) is placed surrounding a base of the tongue and secured to the jaw by reason at an attachment member (element 20 in FIG. 6 of the '171 patent). In the method of the '171 patent, the member 32 can be shortened to draw the base of the tongue toward the jaw and thereby move the tissue of the base of the tongue away from the opposing tissue of the pharyngeal airway. However, this procedure is often uncomfortable. This procedure, referred to as tongue suspension, is also described in Miller et al., "Role of the tongue base suspension suture with The Repose System bone screw in the multilevel surgical management of obstructive sleep apnea", *Otolaryngol. Head Neck Surg.*, Vol. 126, pp. 392–398 (2002).

Two tongue-based surgeries are compared in Thomas et al., "Preliminary Finding from a Prospective, Randomized Trial of Two Tongue-Based Surgeries for Sleep Disordered Breathing", *Otolaryngology-Head and Neck Surg.*, Vol. 129, No. 5, pp. 539–546 (2003). This article compares tongue suspension (as described above) to tongue advancement (mandibular osteotomy).

Another technique for debulking tissue includes applying radio frequency ablation to either the tongue base or of the soft palate to debulk the tissue of the tongue or palate, respectively. This technique is illustrated in U.S. Pat. No. 5,843,021 to Edwards et al. dated Dec. 1, 1998. RF tongue base reduction procedures are described in Powell et al., "Radiofrequency tongue base reduction in sleep-disordered breathing: A pilot study", *Otolaryngol. Head Neck Surg.*, Vol. 120, pp. 656–664 (1999) and Powell et al., "Radiofrequency Volumetric Reduction of the Tongue—A Porcine Pilot Study for the Treatment of Obstructive Sleep Apnea Syndrome", *Chest*, Vol. 111, pp. 1348–1355 (1997).

A surgical hyoid expansion to treat OSA is disclosed in U.S. Pat. No. 6,161,541 to Woodson dated Dec. 19, 2000. Other tongue treatments for OSA include stimulation of the hypoglossal nerve. This procedure is described in Eisle et al., "Direct Hypoglossal Nerve Stimulation in Obstructive Sleep Apnea", *Arch. Otolaryngol. Head Neck Surg.*, Vol. 123, pp. 57–61 (1997).

III. SUMMARY OF THE INVENTION

According to a preferred embodiment to the present invention a method and apparatus are disclosed for treating a condition of a patient's airway. The condition is attributed at least in part to a spacing of tissue from opposing surfaces in the airway. In one embodiment, the method and apparatus include placing a tissue tensioner within the tissue (e.g., within the tongue. Other embodiments show placement of stiffening elements in the tongue near a base of the tongue. The stiffening elements may be tissue-crimping members. The elements are also described as fibrosis-inducing members near the tongue base. Further embodiments include method and apparatus to advance a hyoid bone or epiglottis cartilage of the patient.

IV. BRIEF DESCRIPTION OF THE DRAWINGS

FIG. 1 is a side elevation, schematic view of a patient illustrating structure defining an upper airway of the patient and showing an implant according to an embodiment of the present invention positioned within the soft palate and secured to the bony structure of a hard palate and showing a similar implant in the tongue and secured to the bony structure of the jaw;

FIG. 2 is the view of FIG. 1 following contracting of the implants in the palate and tongue;

FIG. 9 is a view similar to FIG. 7 showing immediate post-implant of a still further embodiment of the present invention;

FIG. 10 is the view of FIG. 9 following tissue in-growth and resorption of bio-resorbable elements;

FIG. 16 is the view of FIG. 14 showing the crimps in a crimped state;

FIG. 16A is a top plan view of a tongue showing an anterior-posterior axis (A-P) and illustrating and alternative orientation of the crimp of FIGS. 14–16;

FIG. 17 is a perspective view of the crimp in the state of FIG. 16;

V. DESCRIPTION OF THE PREFERRED EMBODIMENT

Figure 3:
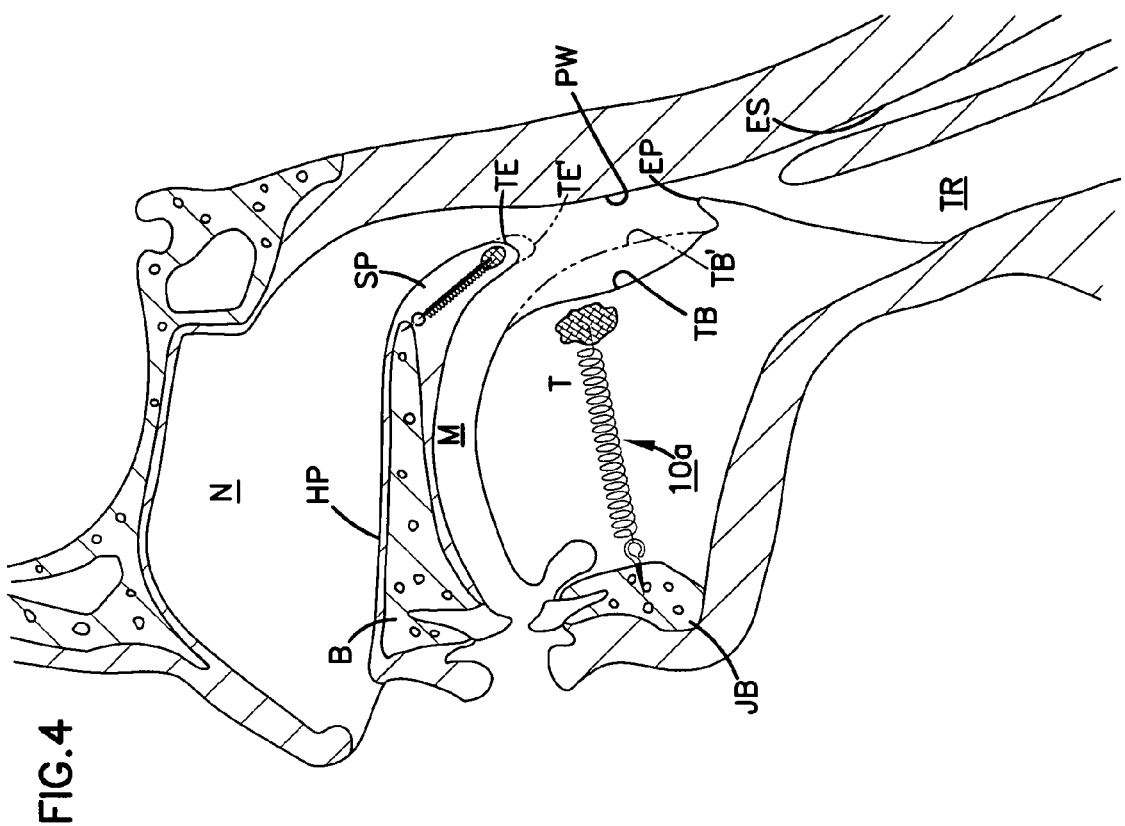
FIG. 3 is a view similar to that of FIG. 1 and showing an alternative embodiment of the present invention with implants of the alternative embodiment implanted in both the soft palate and tongue.

With reference now to the various drawing figures in which identical elements are numbered identically throughout, a description of the preferred embodiment of the present invention will now be provided. To facilitate a description and an understanding of the present invention, the aforementioned U.S. Pat. Nos. 6,250,307; 6,523,542; 6,431,174; 6,601,584; 5,988,171 and 5,843,021 are hereby incorporated herein by reference.

A. Disclosure of Parent Application

The following is the disclosure of U.S. patent application Ser. No. 10/698,819 filed Oct. 31, 2003 with additional remarks:

With initial reference to FIG. 1, a soft palate SP is shown in side elevation view extending from a bony portion of a hard palate HP. The soft palate SP extends rearward to a trailing end TE. FIG. 1 also illustrates a tongue T with a base TB opposing a pharyngeal wall PW. A jawbone JB is shown at the lower front of the tongue T.

As a first described embodiment of the present invention, an implant 10 is shown in FIG. 1 completely implanted within the tongue T. A similar implant 10' is fully implanted in the soft palate SP. As will be apparent, implants 10, 10' are functionally and structurally similar differing only in size to facilitate placement in the tongue T and soft palate SP, respectively. As a result, a description of implant 10 will suffice as a description of implant 10' (with similar elements similarly numbered with the addition of an apostrophe to distinguish the implants 10, 10'). Further, while both implants 10, 10' are shown implanted in the same patient, either could be separately implanted.

The implant 10 includes an elongated member 12 having a tissue in-growth end 14 and a static end 16. The tissue in-growth end 14 may be any tissue growth inducing material (e.g., felt or PET) to induce growth of tissue into the end 14 to secure the end 14 to surrounding tissue following implantation. The elongated member 12 may be suture material one end secured to the felt 14 and with the static end 16 being a free end of the suture material 12.

An anchor 18 (shown in the form of a treaded eye-bolt although other fastening mechanisms could be used) is secured to the jawbone JB. In the case of implant 10', the anchor 18' is secured to the bone of the hard palate. The end 16 is secured to the anchor 18.

The end 14 is placed in the tongue near the tongue base TB. A surgeon adjusts a tension of the suture 12. This causes the tongue base TB to be urged toward the jawbone JB thereby placing the tissue of the tongue in compression. When a desired tension is attained, the surgeon may tie off the static end 16 at the bolt 18 retaining the tissue of the tongue T under tension. This method and apparatus provides a resistance to movement of the tongue base TB toward the pharyngeal wall PW. Similarly, with implant 10', the trailing end TE of the soft palate SP is urged away from the back of the throat and the soft palate SP is prevented from lengthening.

In the foregoing as well as all other embodiments in this application, one member 14 is shown. It will be appreciated that multiple member could be placed in the tongue T.

The embodiments of the present application show an anchor placed in the front center of the jawbone JB. It will be appreciated in this and all other embodiments, the anchor can be placed in other locations (for example, two anchors can be placed on opposite sides of the jaw bone with separate elongated members (e.g., elements 12, 10a, 172, 190 or 190' in the various figures) extending from each anchor.

Placing the implants 10, 10' under tension as in FIG. 1 provides therapy in that the tongue base TB and soft palate trailing end TE are retained from movement toward the pharyngeal wall PW. In addition, at time of initial implantation or thereafter, a surgeon may obtain access to anchors 18, 18' and further shorten the length of the elongated member 12 (i.e., by pulling the member 12 through the bolt 18, 18') to draw the tongue base or trailing end away from the pharyngeal wall to a new profile. This is illustrated in FIG. 2 with the contracted profile shown in solid lines TB, TE and contrasted with the original profile shown in phantom lines TB', TE'.

Figure 4:
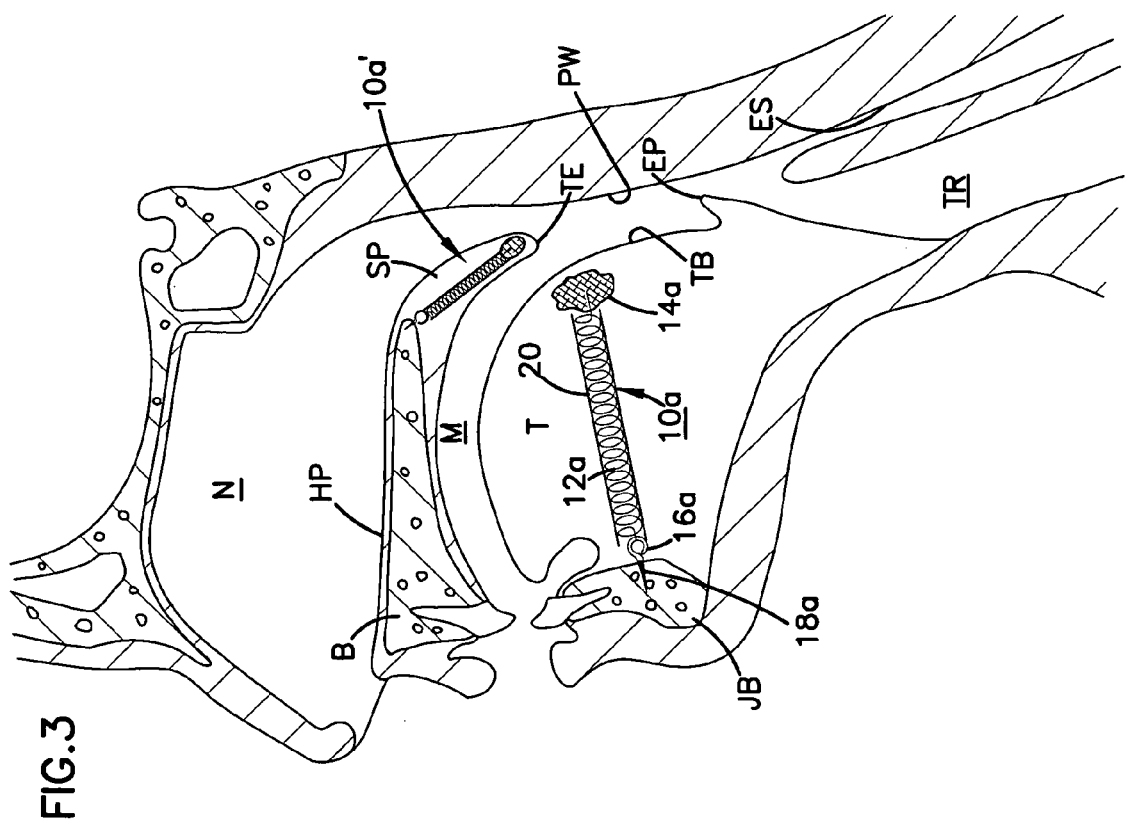
FIG. 4 is the view of FIG. 3 showing the implants in a contracted state.

Referring to FIGS. 3 and 4, an alternative embodiment of the present invention is shown as an implant 10a for the tongue T or implant 10a' for the soft palate SP. As with the embodiments of FIGS. 1 and 2, implants 10a, 10a' are functionally and structurally similar differing only in size to facilitate placement in the tongue and soft palate, respectively. As a result, a description of implant 10a will suffice as a description of implant 10a' (with similar elements similarly numbered with the addition of an apostrophe to distinguish the implants 10a, 10a'). Further, both implants 10a, 10a' are shown implanted in the same patient. Either or both implants could be implanted.

Implant 10a includes a tissue engaging end 14a and static end 16a. As in the embodiment of FIG. 1, the static end 16a is secured to a hard palate at the eyelet of an eyebolt 18a secured to the jawbone JB. Again, as in the embodiment of FIG. 1, the tissue-engaging end 14a may be any material which encourages tissue in-growth and attachment to tissue. An example of such a material may be PET or a felt material.

The tissue engaging end 14a and the static end 16a are connected by a resilient elongated member 12a which may be in the form of a spring member such as nitinol or other member which may be stretched to create a bias urging ends 14a, 16a toward one another. Opposing the bias of the spring member 12a is a bioresorbable material 20 positioned between the tissue-engaging end 14a and the bolt 18a.

After placement of the implant 10a within the tissue of the tongue and with the end 14a near the tongue base TB, the bio-resorbable material 20 will later resorb into the tissue of the tongue T permitting end 14a to be urged toward bolt 18a by the resilience of the spring 12a. This is illustrated in FIG. 4, where the contracted implant 10a places the tissue of the tongue under tension and urging the tongue base TB away from the pharyngeal wall PW. In FIG. 4, the contracted profile of the tongue base TB (and soft palate trailing end TE) is shown in solid lines and the original profile TB' (TE') is shown in phantom lines. Normal function of the tongue T is not impaired since the muscles of the tongue T can overcome the bias of the spring member 12a.

Figure 5:
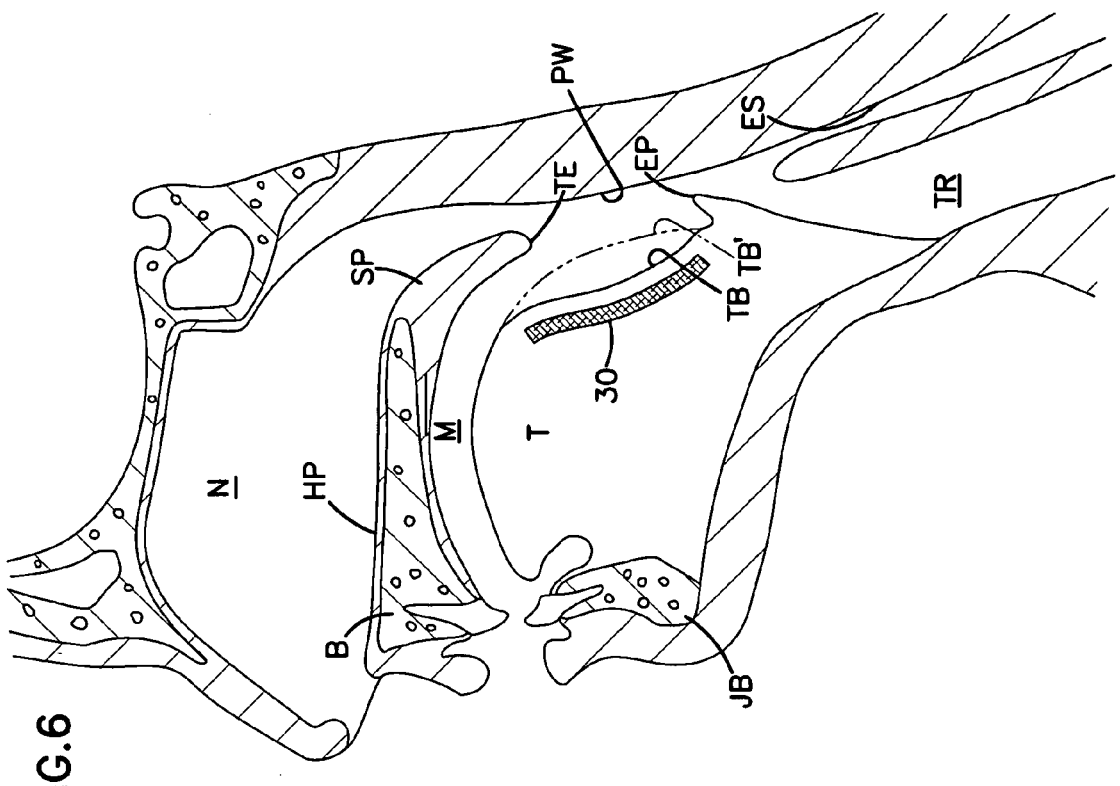
FIG. 5 is a view similar to that of FIG. 1 and showing a further alternative embodiment of the present invention with an implant of the further alternative embodiment implanted in the tongue.
Figure 6:
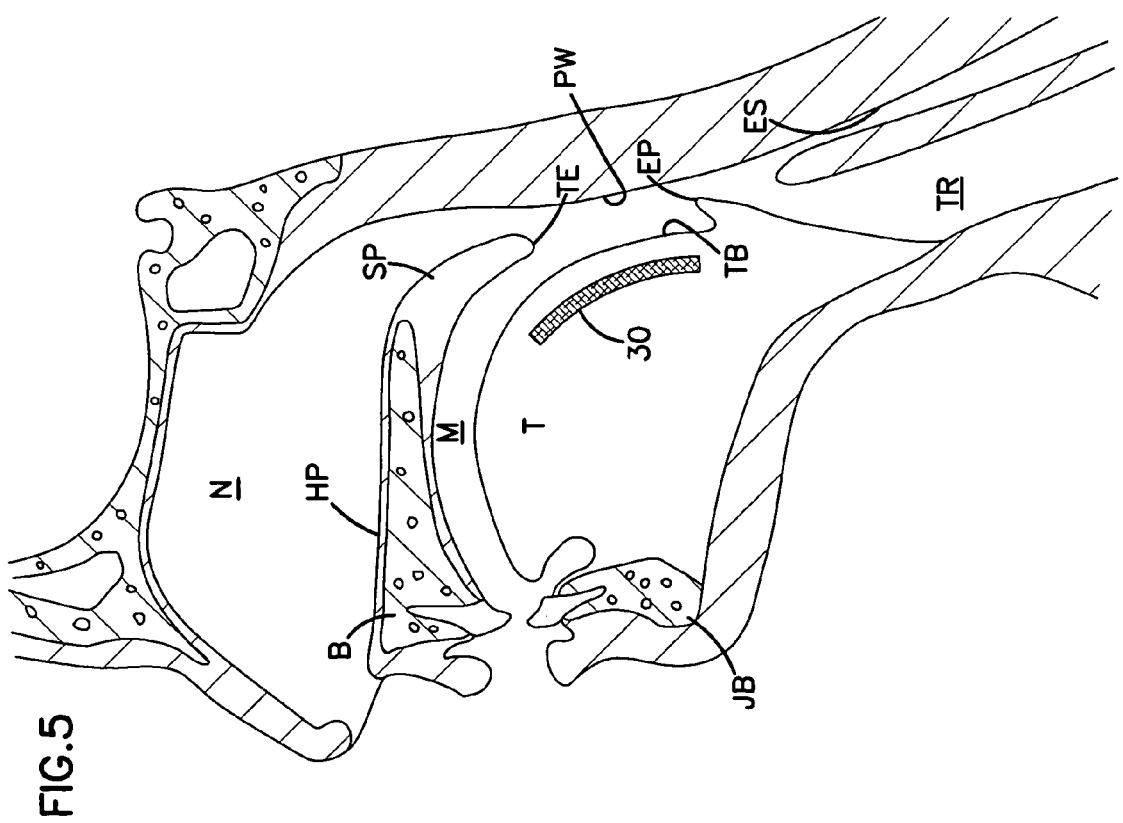
FIG. 6 is the view of FIG. 5 contraction of tissue around the implant.
Figure 7:
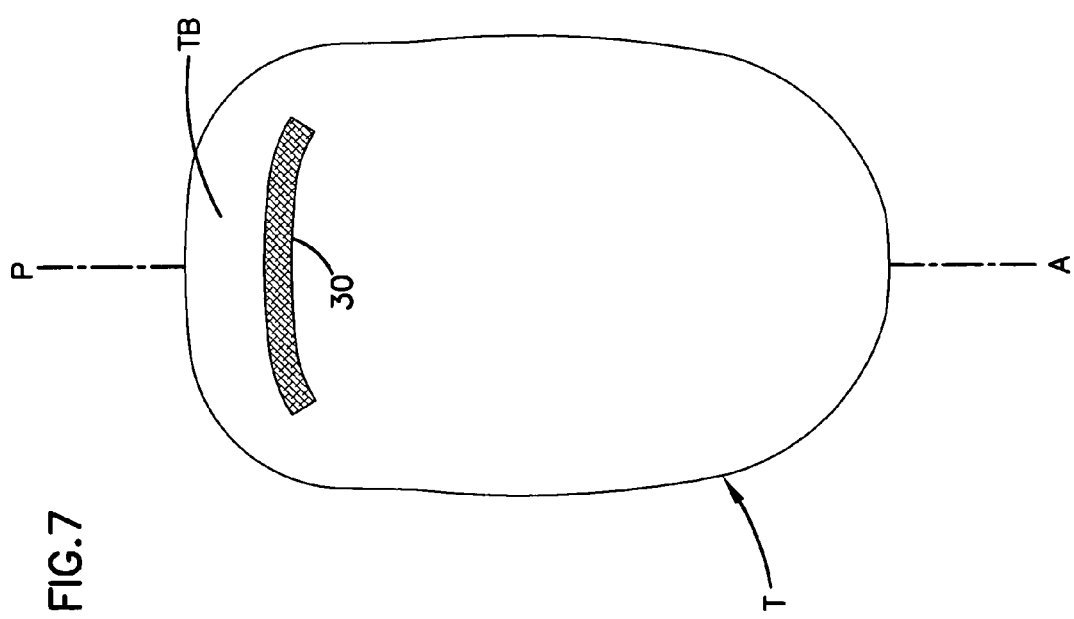
FIG. 7 is a top plan view of FIG. 5 showing an anterior-posterior axis A-P of the tongue.

FIGS. 5–7 illustrate a still further embodiment for reducing the tongue base TB. While term "reducing" is used, it will be appreciated in this and other embodiments that the tongue need not be reduced in volume but can be reshaped are simply displaced by the disclosed inventions to achieve the desired effect. In this embodiment, a sheet 30 of tissue in-growth material (e.g., a sheet of felt with numerous interstitial space) is place in the tongue near the base TB. The sheet 30 is placed beneath the tongue surface and parallel to the base TB substantially covering the area of the tongue base TB. Scarring from the material contracts over time resulting in a reduction in the tongue base as illustrated in FIG. 6. To heighten the amount of tongue base reduction, the sheet 30 may be impregnated with a tissue reducing or stiffening agent (e.g., a sclerosing agent).

FIGS. 9 and 10 illustrate a further variant of FIGS. 5–7. The implant 50 includes three tissue in-growth pads 61, 62, 63. A nitinol bar 64 connects the pads 61–63 in-line with pad 63 centrally positioned. The bar 64 is pre-stressed to have a central bend shown in FIG. 10. Bio-resorbable sleeves 65, 66 hold the bar 64 in a straight line against the bias of bar 64 as in FIG. 9. The implant 50 is implanted as shown in FIG. 9 with the straight bar 64 parallel to the tongue base TB. After implantation, tissue grows into pads 61–63. After the time period of in-growth, the sleeves resorb as in FIG. 10. With the sleeves resorbed, the bar 64 bends to its pre-stressed shape. The tongue base moves with the pad 63 to reposition the tongue base (illustrated in FIG. 10 as the shift from TB' to TB).

Figure 8:
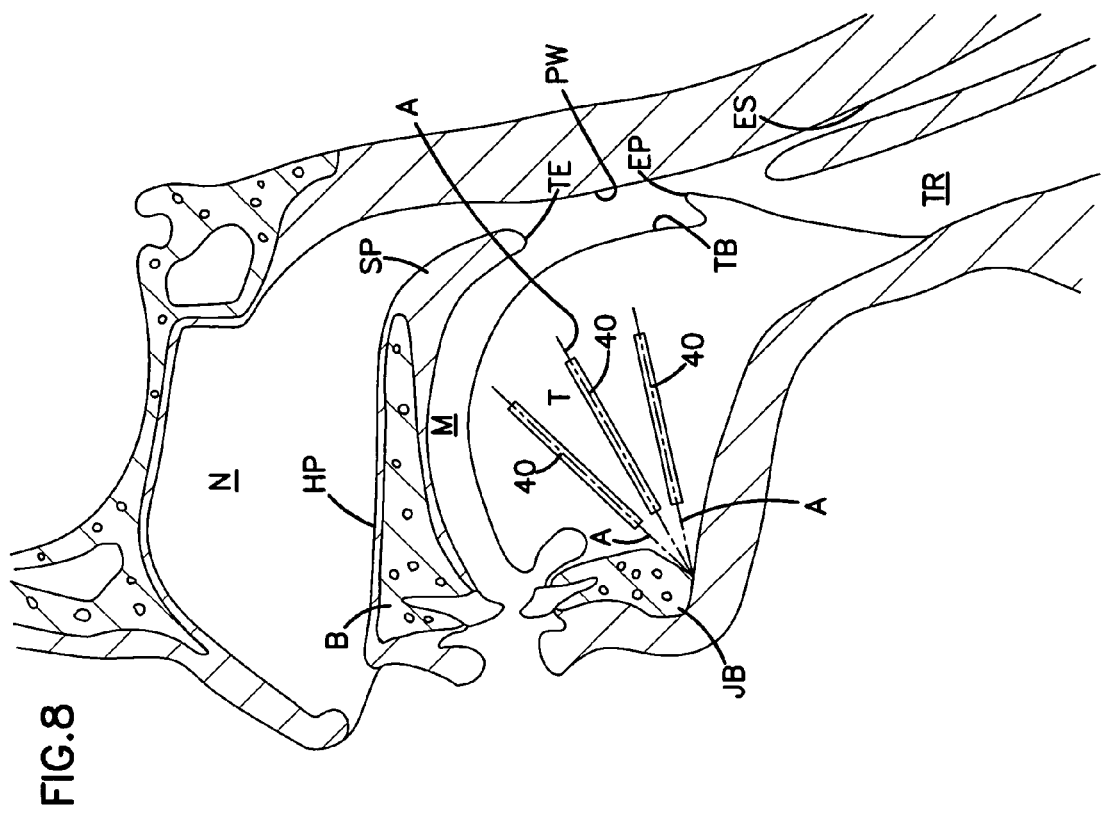
FIG. 8 is a view similar to that of FIG. 1 and showing a yet further alternative embodiment of the present invention with an implants of the yet further alternative embodiment implanted in the tongue.

FIG. 8 illustrates a still further embodiment of the invention for reducing the tongue base. Certain muscles of the tongue (particularly, the genioglossus muscles) radiate from the jawbone JB to the tongue surface as illustrated by lines A in FIG. 8. Contracting implants 40 identical to those in FIGS. 46 and 47 of U.S. Pat. No. 6,601,584 are placed with a contracting axis (the axis between tissue in-growth ends 14a'—identical to ends 102b in FIGS. 46, 47 of the '584 patent) are placed in the tongue in-line with the muscle radiating lines A. Alternatively, the contracting implant 40 may be of the construction shown in FIGS. 48 and 49 of the '584 patent. As the implants contract over time, they urge the tongue from collapsing toward the pharyngeal wall. In lieu of contracting implants, the elongated implants can be static implants such as implants shown in FIG. 11 of U.S. Pat. No. 6,250,307 and labeled 20.

B. Additional Disclosure of Present Application

Figure 11:
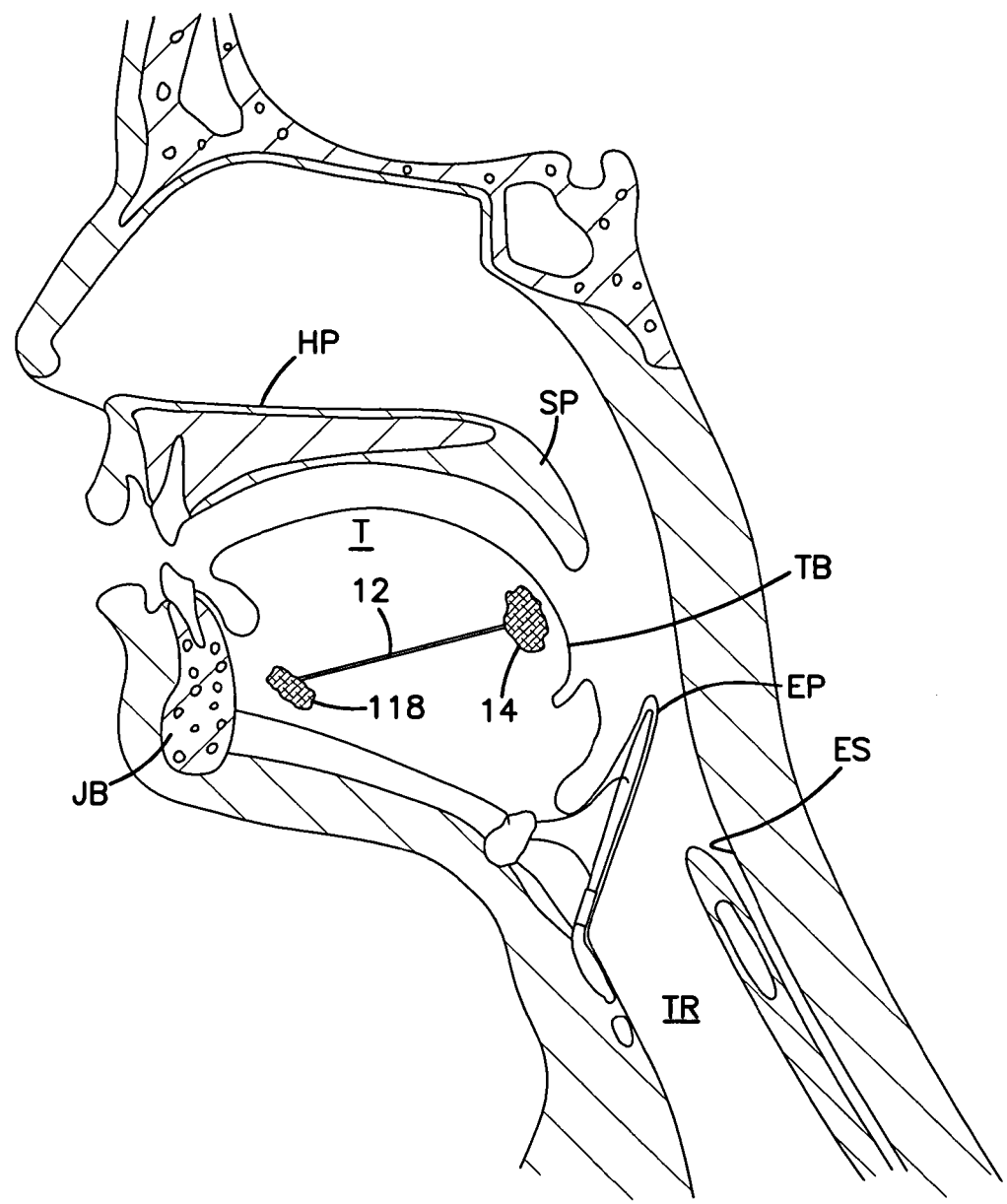
FIG. 11 is a view similar to that of FIGS. 1 and 2 showing an alternative embodiment.

FIG. 11 is a view similar to that of FIGS. 1 and 2 showing an alternative embodiment. Elements in common with those of FIGS. 1 and 2 are numbered identically. The tissue in-growth end 14 is embedded in the tongue T near the tongue base TB. In stead of an anchor 18 in the jaw bone JB as described with reference to FIG. 1, the embodiment of FIG. 11 employs and additional tissue in-growth material 118 embedded in the tongue T near the jaw bone JB. An elongated member 12 (e.g., suture material) acts as a tension member and connects the base tissue in-growth member 14 to the jawbone tissue in-growth member 118. As in the embodiment of FIG. 1, the surgeon can adjust the tension on suture 12. Alternatively, the suture 12 can be replaced with the elements 12a and 20 of FIG. 3.

The tissue in-growth material 118 acts as an embedded anchor and eliminates the need for placement of an anchor 18 in the jawbone JB as described in previous embodiments.

Figures 12, 13:
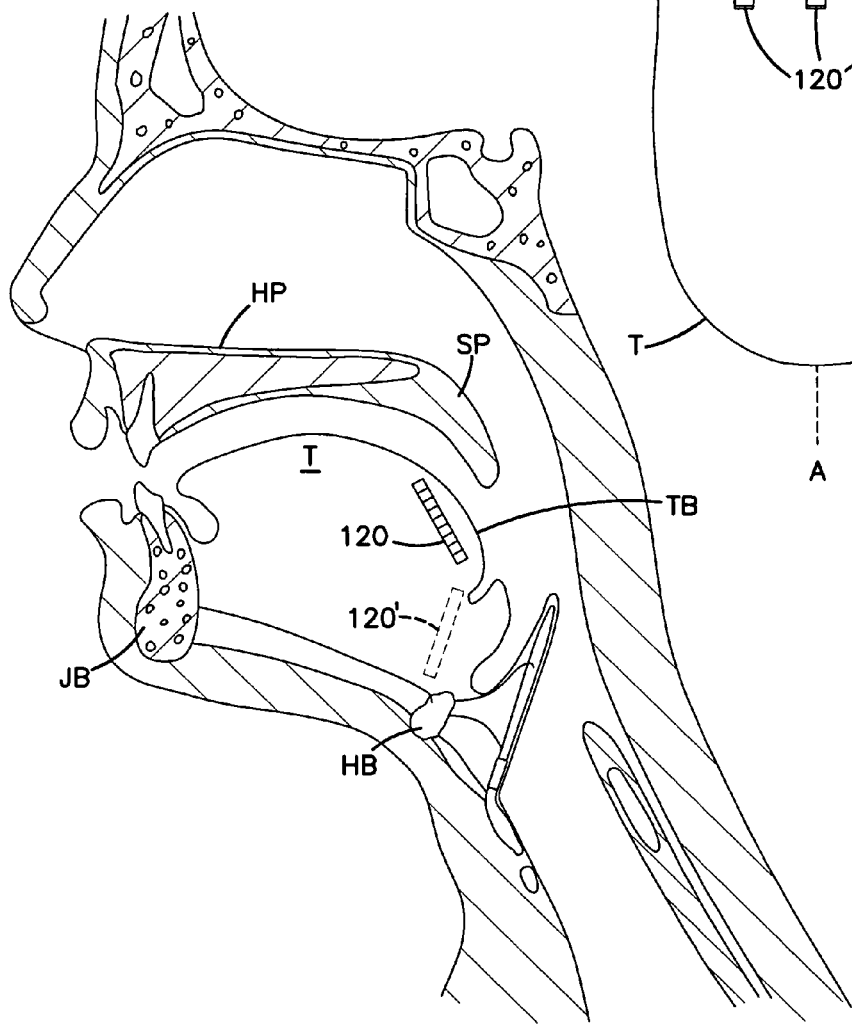
FIG. 12 is the view of FIG. 11 showing a further alternative embodiment of the invention.
FIG. 13 is a top plan view of the tongue of FIG. 12 and shown with reference to an anterior-posterior axis A-P.

FIGS. 12 and 13 show placement of implants 120 in the tongue T near the base TB. Three implants 120 are shown in parallel alignment near the base TB and extending generally parallel to the wall of the tongue base TB. The implants may be polyester braids such as those described in U.S. Pat. No. 6,513,530 to Brenzel et al. dated Feb. 4, 2003 or may be contracting implants such as those described with reference to FIG. 8. The implants 120 tend to stiffen the base of the tongue and resist floppy action or lack of tone in the tissue of the tongue T near the base TB. The implants 120 are spaced apart for fibrosis to interconnect between the implants 120. In FIG. 12, an alternative placement of the implant 120 is shown and illustrated in phantom lines as implant 120'. Implant 120' is positioned near the tongue base TB with one end near the hyoid bone HB and extending upwardly therefrom.

Figure 14:
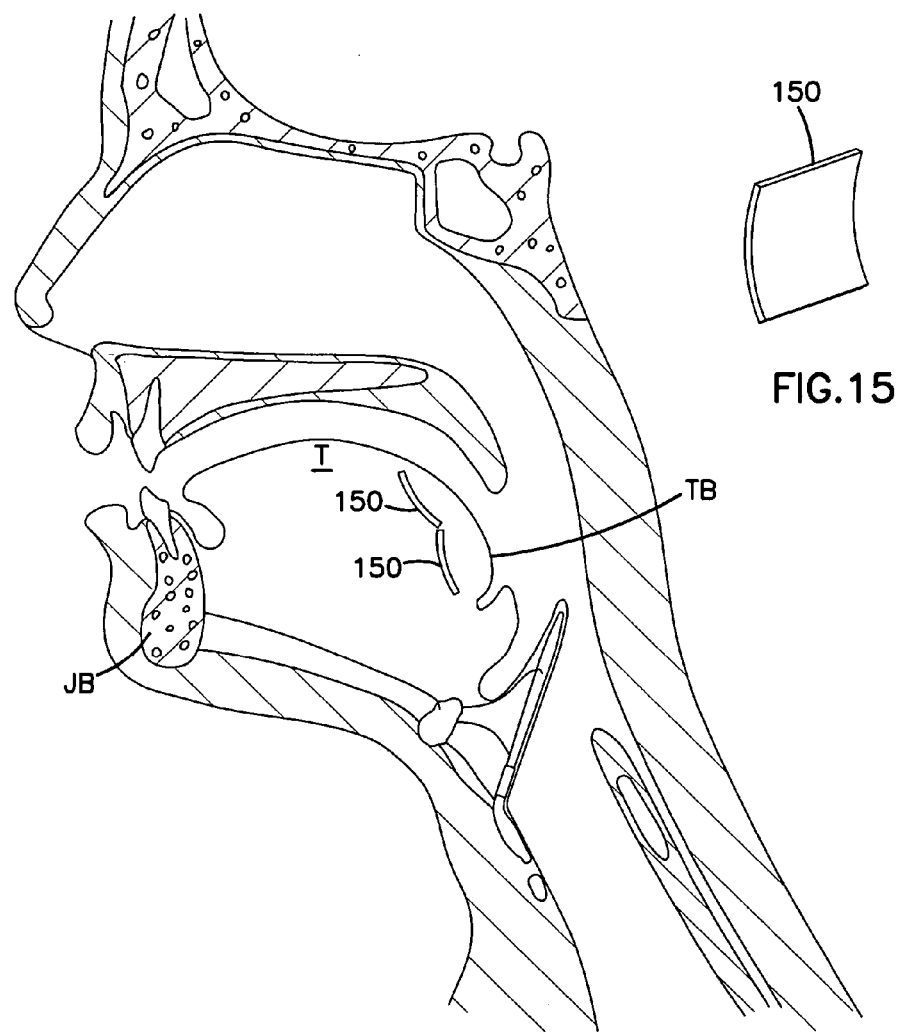
FIG. 14 is the view of FIG. 11 showing a further alternative embodiment of the invention with crimps shown in the tongue in an un-crimped state.
Figure 15:
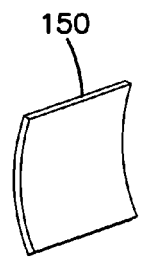
FIG. 15 is a perspective view of the crimp in the state of FIG. 14.

FIGS. 14–17 illustrate the use of imbedded crimps (or staples) to stiffen and potentially reshape the tongue base TB. As illustrated in FIGS. 14 and 15 the crimps 150 are slightly curved members with are placed in the tongue T with concave surfaces opposing the tongue base TB. The crimps 150 are crimped by in situ to a crimped U-shape. The crimping acting squeezes tissue of the tongue to stiffen the tongue. Crimping can also reshape the tongue base TB as illustrated in FIG. 16 (phantom lines illustrating the pre-crimped shape of the tongue base TB). The crimps 150 may be any biocompatible material which plastically deforms to a crimped state. FIG. 16A shows an alternative orientation of the crimp or staples 150. The crimp 150 is rotated 180 degrees from the orientation of FIG. 16 with the crimp 150 at the center of the tongue based TB to result in a crimped in center of the tongue from the original tongue base TB profile shown in phantom lines in FIG. 16A.

Figures 18, 19:
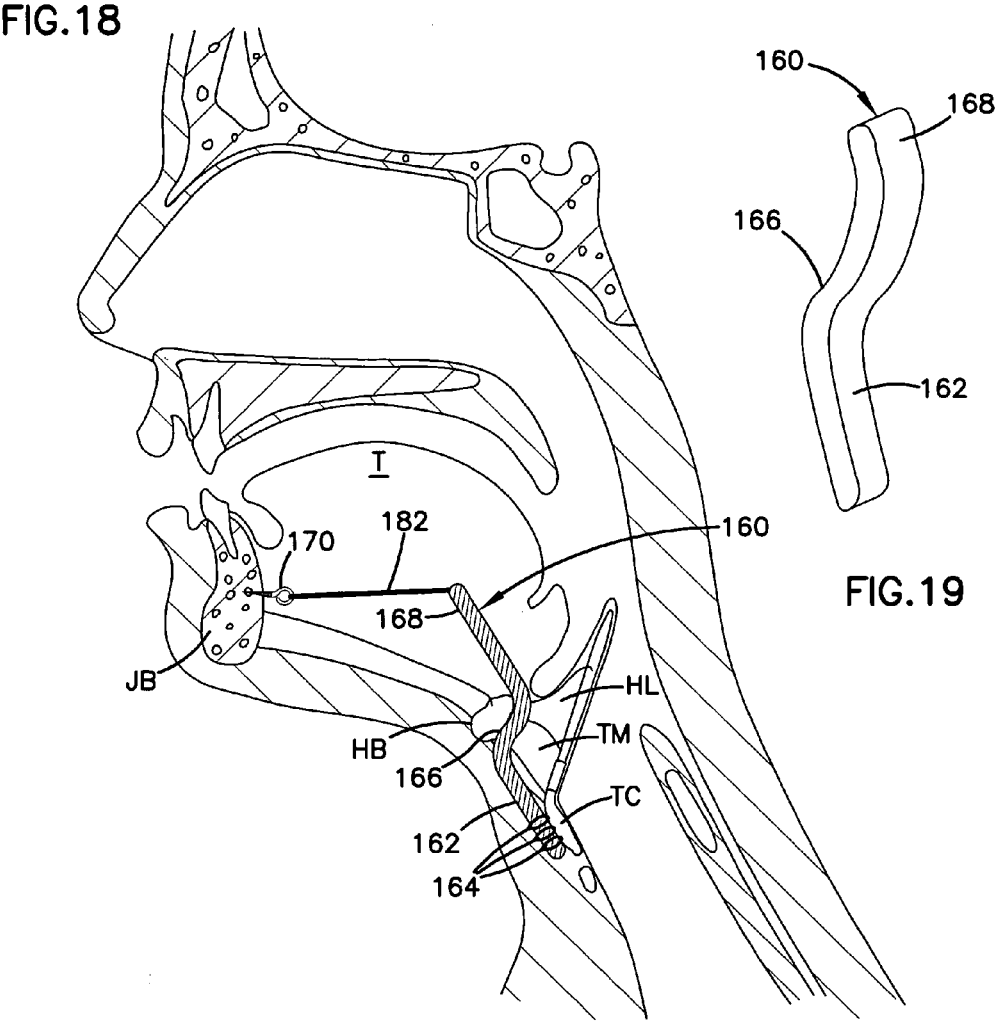
FIG. 18 is the view of FIG. 11 showing a further alternative embodiment of the invention with a lever positioned to advance a hyoid bone of a patient.
FIG. 19 is a perspective view of the lever of FIG. 18.

FIGS. 18 and 19 illustrate an embodiment to advance the hyoid bone (HB). In FIGS. 18 and 19 and lever 160 is provided with a first end 162 adapted to be placed against an anterior surface of thyroid cartilage TC. The end 162 is secured to the thyroid cartilage TC by any suitable means (e.g., sutures 164 or staples or bio-adhesives).

The lever 160 is bent to present an abutting surface 166 which abuts a posterior surface of the hyoid bone HB. The bend of the lever causes it to pass through the thyrohyoid membrane TM and the hyoepiglottic ligament HL.

A second end 168 of the lever 160 extends above the hyoid bone HB and projects into the interior of the tongue T. The second end 168 is secured to an anchor bolt 170 in the jawbone JB by a suture or cable 172 which is placed under tension by a surgeon. The lever 160 urges the hyoid bone forward (i.e., toward the jaw bone JB) with the advantages of the mandibular advancement or mandibular osteotomy procedures.

The lever 160 can be any suitable biocompatible material which has sufficient rigidity to act as a lever of the hyoid bone HB using the thyroid cartilage TC as a fulcrum.

Figure 20:
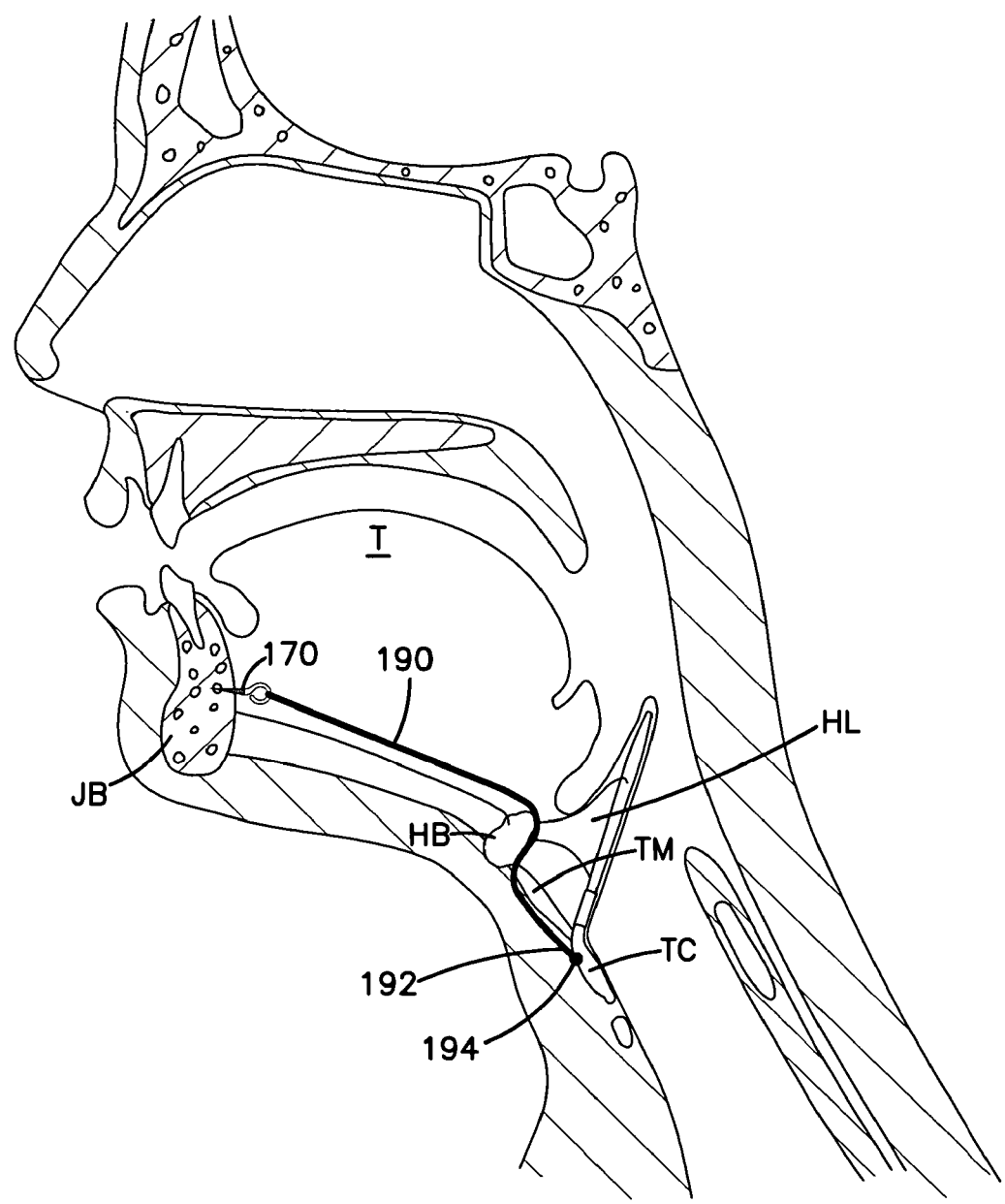
FIG. 20 is the view of FIG. 18 with the lever illustrated as a cable.

FIG. 20 illustrates a similar embodiment with a cable 190 having a first end 192 secured to the thyroid cartilage TC by sutures 194. The cable 190 is passed around the posterior side of the hyoid bone HB (and preferably secured thereto by sutures). A second end of the cable 190 is secured to the anchor 170 in the jawbone JB.

Figure 21:
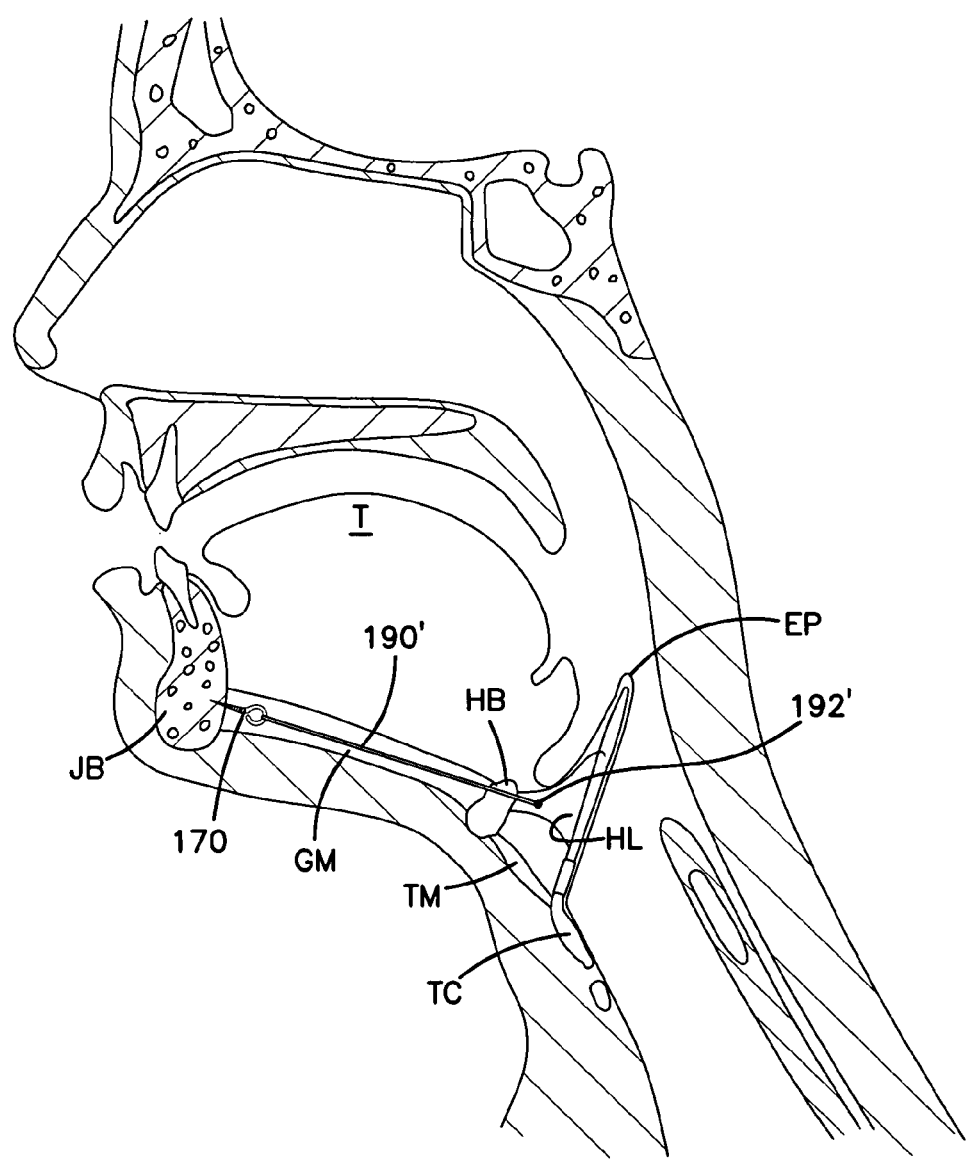
FIG. 21 is the view of FIG. 20 showing a cable secured to an epiglottis cartilage.

FIG. 21 illustrates an alternative embodiment where a cable 190' has a first end 192' secured to the hyoepiglottic ligament HL by sutures. The cable 190' passes into and is affixed to the hyoepiglottic ligament HL. The cable 190' may pass through (as shown) or over the hyoid bone HB. The cable 190' further passes through the geniohyoid muscle GM and terminates at a second end 194' at the jawbone JB where it is secured to an anchor 170.

In each of the embodiments shown in FIGS. 18, 20 and 21, in lieu of a jawbone anchor 170, a tissue embedded anchor (such as anchor 118 in FIG. 11) could be used.

The foregoing describes numerous embodiments of an invention for an implant for the tongue and soft palate to restrict tissue movement toward the pharyngeal wall. Having described the invention, alternatives and embodiments may occur to one of skill in the art. It is intended that such modifications and equivalents shall be included within the scope of the following claims.

What is claimed is:

1. A method for treating a condition of a patient's airway wherein said condition is attributed at least in part to a spacing of a tongue from opposing surfaces in said airway; said method comprising:

placing a tissue tensioner within said tongue, said tensioner including an anterior end and a posterior end joined by a resilient tension member with a spring force resisting motion of said posterior end away from said anterior end while yielding to muscles of the tongue during normal tongue functions;

securing said anterior end to a jaw of said patient and securing said posterior end to tissue of said tongue proximate to a base of said tongue.

2. A method according to claim 1 including shortening a length of said tensioner between said anterior and posterior ends.

3. A method according to claim 2 wherein said tensioner includes a tensioning member between said anterior and posterior ends with said tensioning member retained in a stretched state by a bio-resorbable member selected to resorb after placement of said tensioner in said tissue.

4. A method according to claim 1 wherein said condition is snoring.

5. A method according to claim 1 wherein said condition is sleep apnea.

6. A method according to claim 1 wherein said posterior end is formed of a tissue growth inducing material to induce tissue in-growth into the posterior end following implantation in the tongue.

7. A method according to claim 6 wherein a securing of the anterior end to the jaw bone is performed by accessing the anterior end after initial implantation of the tensioner.

* * * * *